United States Patent [19]  [11] Patent Number: 4,587,284
Lüissi et al. [45] Date of Patent: May 6, 1986

[54] ABSORBENT POLYMER MATERIAL AND ITS PREPARATION

[75] Inventors: Heinz Lüissi, Chur; Peter Geistlich, Stansstad, both of Switzerland

[73] Assignee: Ed. Geistlich Sohne AG fur Chemische Industrie, Lucerne, Switzerland

[21] Appl. No.: 744,615

[22] Filed: Jun. 14, 1985

[51] Int. Cl.$^4$ ............................................. C08F 299/00
[52] U.S. Cl. ........................................ 524/17; 524/18; 524/21; 524/24; 524/28; 524/32; 524/35
[58] Field of Search ............... 525/54.1, 54.23, 54.26; 524/17, 18, 20, 22, 23, 24, 27, 28, 32, 21, 35; 527/201, 207, 312, 314; 260/112 R, 117

[56] References Cited

U.S. PATENT DOCUMENTS

| 3,618,213 | 11/1971 | Shepherd et al. | 424/81 |
| 3,871,376 | 3/1975 | Kozak | 604/291 |
| 3,901,236 | 8/1975 | Assarsson et al. | 604/368 |
| 3,965,091 | 6/1976 | Holst et al. | 536/87 |
| 3,980,084 | 9/1976 | Kross | 128/283 |
| 3,997,484 | 12/1976 | Weaver et al. | 525/54.26 |
| 4,028,290 | 6/1977 | Reid | 524/768 |
| 4,076,663 | 2/1978 | Masuda et al. | 525/54.31 |
| 4,192,727 | 3/1980 | Ward | 204/159.12 |
| 4,200,557 | 4/1980 | Chatterjee et al. | 525/54.23 |
| 4,487,864 | 12/1984 | Bermudez et al. | 524/32 |
| 4,541,871 | 9/1985 | Obayashi et al. | 527/314 |

FOREIGN PATENT DOCUMENTS 1594389  5/1978  United Kingdom .
2036042B 6/1980  United Kingdom .

Primary Examiner—Maurice J. Welsh
Assistant Examiner—Nathan M. Nutter
Attorney, Agent, or Firm—Bernard, Rothwell & Brown

[57] ABSTRACT

An enhanced water-absorbency hydrophilic polymer material, suitable for use in for example wound dressings, is prepared by a process in which a water-containing organic hydrogel comprising a gelable polysaccharide and/or protein or polypeptide interspersed with a polymer of a hydrophilic acrylic or methacrylic acid derivative is permeated with a base, the pH of said hydrogel being raised to at least 9 during treatment with said base.

14 Claims, No Drawings

ABSORBENT POLYMER MATERIAL AND ITS PREPARATION

The invention relates to an absorbent polymer material, more particularly a swellable hydrophilic material, and its preparation.

Materials with high absorbing power for water or other aqueous fluids are of widespread use in a large number of technical, agricultural, medical and cosmetic applications. Their utility is based on their ability to soak up liquid and so immobilize it. If previously saturated with water or an aqueous solution such materials can function as a moisture reservoir.

As long as the volume of liquid to be absorbed is relatively low, a great number of porous and hydrophilic products will be suitable owing to their capillarity. Examples are sawdust, diatomaceous earth, starches, fabrics, and sponges. If, however, larger quantities of liquid are to be absorbed by relatively small amounts of the absorbent material, more effective mechanisms must be evolved. Preferably crosslinked, hydrophilic polymers are then used, since they take up the liquid by swelling. Examples of such products are modified polysaccharides, crosslinked polyacrylic and polymethacrylic acids and their derivatives as well as cross-linked polyvinylalcohols and polyethylene oxides which have low water solubility.

Most of these products, however, lose their mechanical strength and become tacky when the liquid uptake, and hence the swelling, reaches the higher ranges which are of particular interest. Their use is correspondingly limited.

GB-A-1594389 describes the preparation of smooth and strong hydrogels suitable for use as wound dressings by the polymerization of a hydrophilic acrylic or methacrylic acid derivative, e.g. acrylamide, suitably in combination with a crosslinking agent, in a solution of a gelable polysaccharide and/or protein or polypeptide, e.g. in an agar-agar solution.

The hydrogels so formed have a high water content and in GB-A-2036042 it was proposed that the hydrogels of GB-A-1594389 could be dried to a more readily storable form which can be reconstituted to the original swollen hydrogel by soaking.

While our experiments have confirmed that such dried hydrogels could be restored to a swollen form, we have found that irrespective of the drying conditions the dry material loses a significant part of its original swelling ability, its value as an absorbent material being accordingly reduced.

We have now surprisingly found that if the hydrogel is treated with a strong base before drying, not only is the loss of swelling power avoided but the swelling power, i.e. absorbance, may even be increased to a level far above that for the undried hydrogel.

Thus in one aspect the invention provides a process for preparing a hydrophilic polymer material in which a water-containing organic hydrogel comprising a gelable polysaccharide and/or protein or polypeptide interspersed with a polymer of a hydrophilic acrylic or methacrylic acid derivative is permeated with a base, the pH of said hydrogel being raised to at least 9 during treatment with said base, whereby the ability of said hydrogel to retain or absorb aqueous media is increased.

In a further aspect the invention provides the hydrophilic polymer material produced by the process of the invention, in either the dry state or swollen with water or other aqueous fluid.

The water-containing organic hydrogels, treated in the process of the invention are preferably hydrogels of the type described in GB-A-1594389. Thus the hydrophilic acrylic or methacrylic acid derivative is preferably an amide, more preferably acrylamide, or an ester with a polyhydric alkanol, preferably a $C_{1-6}$ alkanol having 3 or more hydroxyl groups, e.g. glycerol, erythritol or pentaerythritol. As cross-linking agents conventional cross-linking agents containing at least two double bonds may be used, for example N,N'-methylene-bis-acrylamide.

The gelable polysaccharide is preferably agarose or agar-agar while amongst gelable proteins and polypeptides gelatine is preferred.

The hydrogel, excluding its aqueous components, preferably comprises 10 to 90% by weight of the acrylic or methacrylic polymer, and 90 to 10% by weight of the polysaccharide, protein or polypeptide. Particularly preferably, the hydrogel comprises 60 to 90% by weight of the acrylic or methacrylic polymer.

The hydrogels are preferably transparent, so that where the hydrophilic polymer material of the invention is to be used as a wound dressing the state of the wound can be observed through the dressing, and may optionally contain reinforcing material such as threads or mesh, or therapeutically active material.

In the process of the invention the hydrogel, such as one prepared according to GB-A-1594389, is preferably washed with water before being contacted with the base. The base can be organic or inorganic; suitable bases including alkali metal hydroxides, quaternary ammonium hydroxides, ammonia, water-soluble organic amines and mixtures thereof. The choice of suitable amines is wide although their pKa values should appropriately be at least 8. The amino group may be primary, secondary, tertiary or member of a heterocyclic ring. The substitutents on the nitrogen atom may be aliphatic or alicyclic moieties. Amines with molecular weights below 100 are preferred.

Permeation with the base can be performed by applying the bases directly to the surface of the hydrogel, for instance by spraying and mixing. With ammonia, amines which are gaseous at temperatures of up to 80° C., and especially suitably amines having boiling points no greater than 70° C., or with other bases showing high vapour pressure at such temperatures, the hydrogel may be treated by storing in an atmosphere containing the base as a gas or a vapour. However, the most preferred method of treatment comprises soaking the hydrogel in an aqueous solution of the base.

Suitable aqueous solutions in which the hydrogel may be soaked include solutions containing at least 0.2% by weight of an alkali metal hydroxide, solutions containing at least 0.5% by weight of ammonia, and solutions containing at least 1.0% by weight of an organic amine.

Where permeation of the hydrogel is to be achieved using a gaseous base, this can be performed at ambient, reduced or elevated pressures.

The base treatment of the hydrogel can be performed in a single stage using one or more bases or alternatively may be performed in several stages using the same or different bases. Furthermore, and especially where the hydrogel is treated with a base in solution, the hydrogel may be treated with other materials such as those set out hereinafter. Thus for example further solvents can be added to improve the efficiency of the base permeation and therapeutically active agents can be added so that the product of the invention is impregnated with such active agents which it will release when used for example as a wound dressing.

When base treatment is by aqueous solution, it should be realised that the hydrogel may swell to absorb much of the solution and that therefore a larger quantity of water must be evaporated in any subsequent drying process. It is therefore preferable to use the only minimum of aqueous base solution necessary to achieve the required permeation and consequently to use such solutions relatively concentrated in order to achieve the required pH of at least 9 thoughout the hydrogel.

The permeation of the hydrogel with the base preferably is performed at temperatures between 0° C. and 40° C., especially preferably at ambient temperature.

The treatment normally lasts from 10 to 50 hours. After only one hour a marked increase in swelling power is already observed. On the other hand no fundamental restriction to the length of the treatment has been found: the swelling power of the product approaches a limiting value with increasing treatment time, so that prolongation of the treatment becomes increasingly pointless.

After treatment with the base, the hydrogel advantageously is dried to produce a hydrophilic polymer material capable of absorbing large quantities of water or aqueous solutions.

Drying may be continued to remove substantially all of the water, to yield a product of very high absorptive capacity, or only part of the water may be removed, to yield a product having lower absorptive capacity but which may be more physiologically compatible. In this respect, partial drying of the base-treated hydrogel to a solids content of from 4 to 8% by weight is particularly preferred.

Drying is preferably effected at temperatures not exceeding 80° C., generally between 0° C. and 80° C., and especially preferably between 40° and 50° C. Higher drying temperatures reduce the swelling power while at lower temperatures the drying process is slowed down. Apart from these limitations, conventional drying methods and equipment may be used.

If highly volatile bases, such as ammonia or low molecular weight amines, are used for the base treatment, these bases evaporate during drying and may be recovered from the vapour leaving the resulting product substantially neutral. This effect is particularly useful in cosmetic, medical and other applications, where a neutral pH value is desirable. Alternatively, to achieve a desired pH in the end product, the base-treated hydrogel may be washed to remove the excess base before the drying step. In such a washing step, a therapeutically active substance may if desired conveniently be introduced into the hydrogel. However, such washing inevitably increases the amount of water which may need to be removed in a drying step and consequently it is preferred to use a volatile base such as ammonia so that no washing is required.

The hydrophilic material of the invention may have a variety of shapes and sizes depending on the use to which it is to be put. Thus for example the material may be in block, rod, sheet, strip, string, granular or pulverulent form. The desired shape can be achieved either by producing the hydrogel in the desired form before it is base-treated and dried or by cutting, grinding or otherwise modifying the form of the base-treated and dried product. The precise conditions for the base treatment and drying process steps will of course need to be adapted to suit the form in which the hydrogel is being treated. Such modification is however well within the capabilities of a person skilled in the art.

Where the hydrophilic materials of the present invention are in the form of blocks, rods, sheets, strips or strings, it is preferred that the materials in at least one dimension be no more than 5 cm, especially preferably from 0.5 to 5 mm, e.g. about 1 cm, in the fully swollen state. When in powder or granule form, it is preferred that the average particle size in the dried state is not greater than 2 mm, and is especially preferably 0.1 to 0.5 mm.

In one preferred aspect the base-treated and dried material of the invention may be ground to produce powders having high absorbencies for aqueous liquids.

When the dry hydrophilic materials according to the invention are soaked in an aqueous solution, smooth gels of moderate strength are obtained, whose weights and volumes can be substantially higher than those achieved by saturation of the untreated hydrogels. Powders prepared following the present invention form smooth, slightly granular pastes when reswollen in aqueous solutions. These pastes retain a part of their absorbing power as long as the volume of liquid added is kept below the saturation volume.

It is particularly advantageous to prepare a dried hydrogel by the above procedure and to comminute this to a powder which is then re-swollen to introduce a controlled amount of water or aqueous solution. The final product preferably has a solids content of from 2 to 20% by weight, especially preferably from 4 to 8% by weight and particularly preferably about 6.5% by weight. The partially hydrated product having a solids content of about 6.5% by weight will generally be capable of absorbing at least about 50% of its own weight of water or other aqueous fluids and will be capable of releasing any physiologically active or beneficial substances that have been pre-absorbed into it.

The physiologically active substances which may advantageously be absorbed into the hydrogel include electrolytes such as physiological saline, calcium, magnesium and/or potassum ions and zinc ions (which have a beneficial effect on cell growth). Amino acids may be present as nutrients, e.g. for skin care or wound alimentation. Zinc ions may of conveniently be incorporated as a zinc salt of an acidic amino acid, e.g. zinc aspartate or zinc taurine, although zinc sulphate may be a suitable source of zinc ions. The hydrogel may also usefully contain one or more antibacterial substances such as antiseptics or antibiotics, which may advantageously be methylol transfer agents such as taurolidine and taurultam which also exert an antitoxaemic effect.

A particularly preferred additive is zinc aspartate which may advantageously be present in the final product at a concentration, based on zinc ions, of 0.01 to 0.5% by weight, preferably 0.1 to 0.25%.

The physiologically active substance can be introduced by swelling the dried hydrogel with a solution of the active substance, or the latter in dry powdered form may be admixed with the dry powdered hydrogel and with the mixture then being swollen with water or an aqueous solution.

The hydrophilic materials of the invention may be used in many applications where high water absorbency is required, for example wound dressings, sanitary napkins and tampons, diapers and cosmetic and pharmaceutical preparations.

The following non-limiting Examples are provided to illustrate the present invention (percentages and parts are by weight unless otherwise indicated):

EXAMPLE 1

20 g of agar-agar are suspended under agitation in 880 g of deionized water and heated to 95° C. until complete dissolution. 1 l of a second aqueous solution containing 70 g of acrylamide and 1.84 g of N,N'-methylene-bis-acrylamide is prepared at ambient temperature and added to the first solution with thorough mixing. Under continued agitation, 2.2 g of N,N,N',N'-tetrakis-(2-hydroxypropyl)-ethylene diamine dissolved in 60 g of water and then 1.26 g of ammonium peroxydisulfate dissolved in 40 g of water are added.

The mixture has a temperature between 50° C. and 55° C. and begins to polymerize immediately. After 10 minutes the gel point is reached. The batch is allowed to cool down overnight during which time polymerization is completed.

The pale yellow, slightly turbid gel is cut into small 5 mm cubes and freed from soluble impurities by washing with pure flowing water for 24 hours. With this washing the gel swells to 135 % of its original weight.

100 parts by weight of washed gel are treated by soaking with 20 parts by weight of 10% aqueous ammonia solution for different lengths of time. After the treatment, excess liquid is drained off.

EXAMPLE 2

The washed gels of Example 1 are dried in a circulating air oven at 50° C. The dried product is ground to particle sizes smaller than 0.315 mm.

For the measurement of water absorption, a hollow plastic cylinder 23 mm in diameter and 50 mm in length, closed at one end with a fine nylon sieve, is used. 100 mg of dried gel powder are placed within the cylinder on the sieve and that end of the cylinder is immersed in distilled water. The water enters the cylinder through the sieve and the powder swells sucking the liquid up above the level of the surrounding water. After 5 minutes the cylinder is placed on dry filter paper to allow excess water to drain away. After 6 minutes have elapsed the weight of the wet gel powder is determined. The weight ratio of wet to dry gel is used to characterize the absorbency.

The following results have been obtained:

| Duration of treatment with 10% ammonia | Absorbency |
| --- | --- |
| no treatment | 13.8 |
| 1 hour | 22.2 |
| 4 hours | 28.4 |
| 9 hours | 36.7 |
| 20 hours | 43.3 |
| 30 hours | 48.2 |

EXAMPLE 3

The methods described in Example 1 were used to prepare a hydrogel which was treated by soaking for 20 hours with ammonia solutions of different concentrations at a ratio of 20 parts by weight of ammonia solution to 100 parts by weight of washed gel.

EXAMPLE 4

The washed gels of Example 3 were dried at 50° C. and the products obtained were tested as in Example 2. The following results have been obtained:

| Ammonia concentration % by weight | Absorbency |
| --- | --- |
| no treatment | 13.8 |
| 2% | 34.2 |
| 5% | 37.3 |
| 10% | 43.3 |
| 25% | 48.6 |

All samples prepared in Examples 2 and 4 form stiff, slightly granular pastes when added to a smaller amount of water than that corresponding to their absorbency. These pastes show a virtually neutral reaction (pH=7.0 to 7.5) against indicator paper.

EXAMPLE 5

In an analogous fashion to the preparation in Example 1, a hot solution of 10 g of agar-agar in 570 g of water is mixed with a solution containing 31.8 g acrylamide, 0.76 g N,N'-methylene-bis-acrylamide and 0.15 g N,N,N',N'-tetramethylethylenediamine in 357 g of water. Polymerization is started by adding 1.6 g of a 25% solution of ammonium peroxydisulfate. Before the gel point is reached, this mixture is cast between glass sheets separated by rubber gaskets. At the end of the polymerization and cooling period hydrogel sheets with a thickness of 3.5 mm are obtained.

These sheets were washed under running water and agitation with injected air for 24 hours. One portion of the sheets was then directly dried at 45° C.

The other portion was first treated with gaseous ammonia. To achieve this the bottom of a dessicator was covered with a 3 cm deep layer of concentrated 25% ammonia solution.

A washed gel sheet was laid on a stainless steel screen 10 cm above the liquid surface. The dessicator was closed and partially evacuated to remove the air. After 20 hours the treated gel sheet was transferred to a circulating air oven and dried at 45° C.

The dried gel sheets were thin, colourless, clear, slightly brittle films. Their water absorbency was measured by weighing before and during soaking in water at ambient temperature.

| Soaking duration | Absorbency | |
| --- | --- | --- |
| | untreated | treated |
| 15 minutes | 6.9 | 12.3 |
| 30 minutes | 8.8 | 18.0 |
| 1 hour | 10.6 | 24.2 |
| 2 hours | 12.3 | 29.9 |
| 3 hours | 13.1 | 32.8 |
| 20 hours | 14.1 | 35.5 |

The swollen sheets had a smooth, leathery feel. The water uptake of the treated material was 2.5 times higher than that of the untreated film. The effect of swelling on the thickness of the films was much more pronounced than the effect on the two other dimensions.

EXAMPLE 6

250 g samples of washed hydrogel, prepared in accordance with Example 1, were mixed with 50 ml of 1% sodium hydroxide or potassium hydroxide and left for the duration of the base-treatment. The base-treated hydrogels were drained and then dried in a circulating air oven before being tested as in Example 2.

The following results were obtained:

| Base | Treatment duration | Drying temperature | pH before drying | pH after drying | Absorbency |
|---|---|---|---|---|---|
| NaOH | 43 hours | 45° C. | 11.5 | 10.0 | 55.0 |
| KOH | 22 hours | 50° C. | 11.0 | 9.0 | 20.8 |

The pH values were measured in the wet state with colour indicator sticks.

If neutral pH material is required, the base-treated gel for this Example may be washed with flowing water, before the drying stage.

EXAMPLE 7

Analogously to Example 6, 250 g samples of washed hydrogel were treated with different organic bases in various quantities and concentrations, drained, dried and tested.

The following results were obtained:

| Base | Quantity | Concentration | Treatment duration | pH before drying | pH after drying | Absorbency |
|---|---|---|---|---|---|---|
| ammonia | 50 ml | 10% | 50 hrs. | 11.0 | 7.2 | 68.5 |
| ethylamine | 20 ml | 28% | 50 hrs. | 11.0 | 7.2 | 87.1 |
| ethylamine | 20 ml | 70% | 41 hrs. | 12.0 | 7.2 | 95.0 |
| diethylamine | 5 g | 100% | 28 hrs. | 11.0 | 7.5 | 74.0 |
| trimethylamine | 40 ml | 20% | 47 hrs. | 11.0 | 7.2 | 64.5 |
| trimethylamine | 40 ml | 40% | 41 hrs. | 11.0 | 7.2 | 72.3 |
| piperidine | 25 ml | 10% | 28 hrs. | 11.0 | 9.0 | 45.8 |

EXAMPLE 8

Hydrogel is prepared and washed following the procedure described in Example 1.

The batch is divided into two parts. One part is dried immediately in a circulating air blown oven at 45° C. The other part is treated at ambient temperature with 20 parts by weight of concentrated (25%) ammonia solution per 100 parts of hydrogel for 24 hours. It is then dried in the same way. Both samples are ground to particle sizes smaller than 0.315 mm.

To form homogeneous pastes, 6.5 g of the dry hydrogel powders are thoroughly mixed with 93.5 g of an aqueous solution containing 2.98 g (40 mMoles) potassium chloride and 3.33 g (30 m Moles) calcium chloride per liter and the mixture is allowed to equilibrate during storage overnight. The above-mentioned $KCl/CaCl_2$ solution is known for its beneficial effect on wound healing.

The remaining absorbency for water and physiological (0.9%) sodium chloride solution, considered as a valuable model for serum, is determined in the following way:

5.0 g of paste are diluted with an excess (10 ml) of distilled water or physiological saline respectively. After one hour at ambient temperature the mixture is poured into a filtering funnel and the free liquid is drained away. The weight gain of the remaining hydrogel is determined as a percentage of the original weight.

|  | Hydrogel untreated/treated with ammonia | |
|---|---|---|
| Weight gain in water | 48% | 370% |
| Weight gain in physiological saline | 3% | 76% |

EXAMPLE 9

Following the procedures described in Example 8, hydrogel is prepared, treated with ammonia, dried and ground to a powder.

65 parts by weight of the dry hydrogel powder are thoroughly mixed in a ball mill with 1 part by weight of zinc aspartate. 6.6 g of the resultant mixture is transferred to a beaker and there swollen to a smooth gel paste (100 g) by the addition of distilled water (93.4 ml) under stirring with a spatula.

We claim:

1. A process for preparing a hydrophilic polymer material in which a water-containing organic hydrogel comprising a gelable polysaccharide and/or protein or polypeptide interspersed with a polymer of a hydrophilic acrylic or methacrylic acid derivative is permeated with a base, the pH of said hydrogel being raised to at least 9 during treatment with said base, whereby the ability of said hydrogel to retain or absorb aqueous media is increased.

2. A process as claimed in claim 1 in which the hydrogel is agar-agar and the polymer is cross-linked acrylamide.

3. A process as claimed in claim 1 in which the hydrogel comprises 60 to 90% by weight of the acrylic or methacrylic polymer.

4. A process as claimed in claim 1 in which the base is an alkali metal hydroxide or quaternary ammonium hydroxide, ammonia or an amine with a molecular weight below 100.

5. A process as claimed in claim 1 in which the hydrogel is permeated with an aqueous solution containing at least 0.2% by weight of an alkali metal hydroxide, at least 0.5% by weight of ammonia or at least 1.0% by weight of an amine.

6. A process as claimed in claim 1 in which, after base treatment, the hydrogel is dried at a temperature not exceeding 80° C.

7. A process as claimed in claim 6 in which the base is removed before or during drying.

8. A process as claimed in claim 6 in which the dried hydrogel is comminuted to powder or granule form.

9. A process as claimed in claim 6 in which the dried hydrogel is contacted with water or an aqueous solution to yield a hydrogel which is incompletely hydrated and capable of absorbing further water.

10. A process as claimed in claim 9 in which the dried hydrogel is contacted with an aqueous solution containing one or more electrolytes, nutrients, physiologically active polypeptides or proteins and/or antibacterial agents.

11. A process as claimed in claim 9 in which the dried hydrogel is admixed with one or more electrolytes, nutrients, physiologically active polypeptides or proteins and/or antibacterial agents and the resultant admixture is contacted with water or an aqueous solution to yield said incompletely hydrated hydrogel.

12. A process as claimed in claim 9 in which in producing said incompletely hydrated hydrogel there is incorporated into the hydrogel zinc aspartate in an amount sufficient to yield a zinc content in said incompletely hydrated hydrogel of from 0.01% to 0.5% by weight.

13. A hydrophilic polymer material when produced by a process as claimed in claim 1.

14. A hydrophilic polymer material as claimed in claim 13 in paste form containing from 92 to 96% by weight water.

* * * * *